(12) United States Patent
Himmelsbach et al.

(10) Patent No.: US 6,171,648 B1
(45) Date of Patent: Jan. 9, 2001

(54) BACKING MATERIAL WITH PARTIAL SELF-ADHESIVE COATING

(75) Inventors: Peter Himmelsbach, Buxtehude; Peter Jauchen; Klaus Keite-Telgenbüscher, both of Hamburg; Matthias Lehder, Buchholz, all of (DE)

(73) Assignee: Beiersdorf AG, Hamburg (DE)

(*) Notice: Under 35 U.S.C. 154(b), the term of this patent shall be extended for 0 days.

(21) Appl. No.: 09/176,295

(22) Filed: Oct. 21, 1998

(30) Foreign Application Priority Data

Nov. 22, 1997 (DE) ............................................. 197 51 873

(51) Int. Cl.⁷ .................. C09J 7/04; A61L 15/58
(52) U.S. Cl. ...................... 427/208.2; 427/208.4; 428/343; 428/355 BL; 442/150; 442/151
(58) Field of Search .................... 428/195, 343, 428/349, 355 BL, 355 AC; 427/208.2, 208.4; 442/150, 151; 424/448, 449

(56) References Cited

U.S. PATENT DOCUMENTS

| | | | |
|---|---|---|---|
| 4,076,881 | * 2/1978 | Sato | 427/208.2 X |
| 5,322,709 | * 6/1994 | Lulla et al. | 427/208.2 X |
| 5,641,506 | 6/1997 | Talke et al. | 424/443 |

FOREIGN PATENT DOCUMENTS

| | | | |
|---|---|---|---|
| 4308649 | 9/1994 | (DE) | A61L 15/42 |
| 19620107 | 11/1997 | (DE) | C09J 7/04 |
| 0356777 | 3/1990 | (EP) | C09J 7/02 |

OTHER PUBLICATIONS

Derwent–Abstract DE 42 37 252.
espacenet–Abstract DE 42 37 252.
Derwent Abstract of JP 07 300575 (Nov. 14, 1995).
English–language counterpart to DE 196 20 107 (U.S. Serial No. 09/171,175, filed Oct. 14, 1998).
English–language counterpart to EP 0356777 and DE 3829077 (U.S. Serial No. 07/397,618 filed Aug. 23, 1989).

* cited by examiner

Primary Examiner—Daniel Zirker
(74) Attorney, Agent, or Firm—Norris McLaughlin & Marcus P.A.

(57) ABSTRACT

Backing material with a partial self-adhesive coating on at least one side, the application of the self-adhesive composition taking place in the form of geometric structures, wherein for at least some of the geometric structures the base area by means of which the geometric structures adhere to the backing material lies within the area of projection of the geometric structures which is formed as a consequence of the fact that the geometric structures are projected perpendicularly onto the backing material.

7 Claims, 2 Drawing Sheets

BACKING MATERIAL WITH PARTIAL SELF-ADHESIVE COATING

The invention relates to a backing material which has been given a partial self-adhesive treatment on at least one side, having been coated with a self-adhesive composition in the form of geometric structures, to processes for producing the coated backing material and to its use.

The partial coating of backing materials with pressure-sensitive self-adhesive compositions is a known technique, whether the self-adhesive compositions are applied in patterned form, for example by screen printing (DE-C 42 37 252), in which case the domes of adhesive can also differ in their size and/or distribution (EP-B 353 972), or by intaglio printing, in lines which interconnect in the longitudinal and transverse directions (DE-C 43 08 649).

It is also known that backing materials detachable especially without residue can be coated with self-adhesive materials.

DE-A 42 37 252 uses special geometries to achieve the absence of residue.

The doping of partially coated self-adhesive tapes has also been described. US 4,699,792 describes a plaster device of this kind, comprising active substances.

Sheet-like structures which can be redetached without residue are obtainable commercially in block form, inter alia, under the name "tesa Notes"® from Beiersdorf.

As backing materials, numerous materials on a film, foil, woven, knit, nonwoven, gel or foam basis have already been described and are also being employed in practice.

Particular requirements are placed on the backing materials in the medical sector. The materials are required to be compatible with the skin, generally permeable to air and water vapour, and also easy to model and conformable. As a result of these requirements, a very thin or soft backing is frequently preferred. For handling and in use, however, the backing materials are also required to be of sufficient strength and possibly of limited extensibility. Furthermore, the backing material should retain sufficient strength and low extensibility even after becoming wet through.

Specific applications, an example being tapes for functional tape dressings for the prophylaxis and therapy of injuries, disorders and altered states of the locomotor system, require non-elastic backings having high strength in the direction of stress. This is achieved by using wovens, usually of cotton or viscose. Backing materials of this kind, with appropriately high basis weight, are generally costly. High flexibility can be achieved only by means of a woven of relatively low strength. When such a fabric is stressed, however, it generally exhibits a certain degree of extension, which is undesirable for the application.

The advantage of patterned application is that the adhesive materials, given an appropriately porous backing material, are permeable to air and water vapour and, in general, are readily redetachable.

The partial application makes it possible, especially in the case of medical applications, for the transepidermal water loss to be dissipated through regulated channels, and improves the evaporation of perspiration from the skin, especially when the backing materials used are permeable to air and water vapour. This prevents the skin irritations induced by instances of build-up of body fluids. The dissipation channels employed allow such fluids to be conducted away even when a multi-ply dressing is used.

A disadvantage of these products, however, is that if the area covered by the adhesive film, which is impermeable per se, is too large there is a corresponding reduction in the permeability to air and water vapour, and the consumption of adhesive composition rises, and also, if the area covered by the adhesive film is too small, the adhesion properties suffer, i.e. the product is detached too readily from the substrate, in particular from the skin, and especially in the case of heavy, textile backing materials.

In the case of the pressure-sensitive self-adhesive compositions referred to, the compositions may be present in a carrier matrix for the purpose of processing. The term carrier matrix is understood to refer to common organic or inorganic solvents or dispersion media.

Systems without a carrier matrix are referred to as 100% systems and are likewise not unknown. They are processed in the elastic or thermoplastic state. A common mode of processing is that of the hotmelt.

Pressure-sensitive hotmelt adhesive compositions of this kind have also already been described in the prior art. They are based on natural or synthetic rubbers and/or other synthetic polymers.

An advantage of the 100% systems is that they avoid an operation of removing the carrier matrix, i.e. the auxiliary media, thereby raising the productivity of processing and at the same time reducing the expenditure on machinery and the energy costs. In addition, this reduces the occurrence of residues of the carrier matrix, which, in turn, is to the benefit of a reduction in the allergenic potential.

The object of the invention was to provide a backing material which is partially self-adhesive on at least one side and which owing to its treatment, i.e. to the applied form and properties of the adhesive composition, and to the material properties of the backing material, serves a functionally appropriate purpose for various fixings, especially for medical products and, in doing so, offers both functional and economic advantages.

This object is achieved by a backing material which is partially self-adhesive on at least one side, as specified in the main claim. The subclaims relate to advantageous embodiments of the backing material, to processes for producing the backing material, and to particularly advantageous uses.

The invention accordingly provides a backing material with a partial self-adhesive coating on at least one side, the application of the self-adhesive composition taking place in the form of geometric structures. For at least some of the geometric structures the base area by means of which the geometric structures adhere to the backing material lies within the area of projection of the geometric structures which is formed as a consequence of the fact that the geometric structures are projected perpendicularly onto the backing material.

Within the geometric structures, therefore, there is at least one cross-sectional area which is aligned parallel to the backing material and which is greater than the base area, i.e. the area by which the geometric structures are anchored to the backing material.

Suitable backing materials are all rigid and elastic sheet-like structures composed of synthetic and natural raw materials. Preference is given to backing materials which, following the application of the adhesive composition, can be employed in such a way that they fulfil the characteristics of a functional bandage. Examples are textiles such as wovens, knits, lays, nonwovens, laminates, nets, films, foams and papers. In addition, these materials can be pretreated or aftertreated. Common pretreatments are corona and hydrophobicization; customary aftertreatments are calendering, thermal conditioning, laminating, punching and lining.

For the coating of the backing it is possible with advantage to employ thermoplastic hotmelt adhesive compositions based on natural and synthetic rubbers and on other synthetic polymers such as acrylates, methacrylates, polyurethanes, polyolefins, polyvinyl derivatives, polyesters or silicones with corresponding additives such as tackifier resins, plasticizers, stabilizers and other auxiliaries where necessary.

Their softening point should be higher than 50° C., since the temperature of application is generally at least 90° C. and preferably between 120° C. and 150° C., or between 180° C. and 220° C. in the case of silicones. Postcrosslinking by means of UV or electron-beam irradiation may be appropriate, if desired, in order to establish particularly advantageous properties of the hotmelt adhesive composition.

Hotmelt adhesive compositions based on block copolymers, in particular, are notable for their diverse variation options, since the controlled reduction in the glass transition temperature of the self-adhesive composition as a result of the selection of the tackifiers, plasticizers, polymer molecule size and molecular distribution of the starting components ensures the required bonding to the skin in a manner appropriate to their function, even at critical points of the human locomotor system.

The high shear strength of the hotmelt self-adhesive composition is achieved through the high cohesiveness of the polymer. The good tack results from the range of tackifiers and plasticizers employed.

For systems which adhere particularly strongly, the hotmelt self-adhesive composition is based preferably on block copolymers, especially A-B or A-B-A block copolymers or mixtures thereof. The hard phase A is primarily polystyrene or its derivatives and the soft phase B comprises ethylene, propylene, butylene, butadiene, isoprene or mixtures thereof, particular preference being given to ethylene and butylene or their mixtures.

However, polystyrene blocks may also be present in the soft phase B, in an amount of up to 20% by weight. The overall proportion of styrene, however, should always be less then 35% by weight. Preference is given to styrene contents of between 5 and 30%, since a lower styrene content makes the adhesive composition more conforming.

The controlled blending of diblock and triblock copolymers is particularly advantageous, preference being given to a proportion of diblock copolymers of less than 80% by weight.

In one advantageous embodiment the hotmelt self-adhesive composition has the composition indicated below:

| | |
|---|---|
| from 10 to 90% by weight of | block copolymers, |
| from 5 to 80% by weight of | tackifiers, such as oils, waxes, resins and/or mixtures thereof, preferably mixtures of resins and oils, |
| less than 60% by weight of | plasticizers, |
| less than 15% by weight of | additives, |
| less than 5% by weight of | stabilizers. |

The aliphatic or aromatic oils, waxes and resins used as tackifiers are preferably hydrocarbon oils, waxes and resins, the consistency of the oils, such as paraffinic hydrocarbon oils, or of the waxes, such as paraffinic hydrocarbon waxes, accounting for their favourable effect on bonding to the skin. Plasticizers used are medium- or long-chain fatty acids and/or their esters. These additions serve to establish the adhesion properties and the stability. If desired, further stabilizers and other auxiliaries are employed.

Filling the adhesive composition with mineral fillers, fibres or hollow or solid microbeads is possible.

The hotmelt adhesive composition has a softening point of more than 70° C., preferably from 95 to 120° C.

Medical backing materials in particular are subject to stringent requirements in terms of the adhesion properties. For ideal application the hotmelt adhesive composition should be possess a high tack. There should be functionally appropriate bond strength to the skin and to the reverse of the backing. So that there is no slipping, the hotmelt adhesive composition is also required to have a high shear strength.

The controlled reduction in the glass transition temperature of the adhesive composition as a consequence of the selection of the tackifiers, of the plasticizers and of the polymer molecule size and of the molecular distribution of the starting components achieves the required bonding, in a manner appropriate to the function, to the skin and to the reverse of the backing.

The high shear strength of the adhesive composition employed here is achieved through the high cohesiveness of the block copolymer. The good tack arises from the range of tackifiers and plasticizers employed.

Product properties such as tack, glass transition temperature and shear stability can be quantified readily using a dynamomechanical frequency measurement. In this case, use is made of a rheometer controlled by shearing stress.

The results of this measurement method give information on the physical properties of a substance by taking into account the viscoelastic component. In this instance, at a preset temperature, the hotmelt self-adhesive composition is set in oscillation between two plane-parallel plates with variable frequencies and low deformation (linear viscoelastic region). Via a pickup control unit, with computer assistance, the quotient (Q=tan δ) between the loss modulus (G", viscous component) and the storage modulus (G', elastic component) is determined.

$$Q = \tan \delta = G''/G'$$

A high frequency is chosen for the subjective sensing of the tack and a low frequency for the shear strength. A high numerical value denotes better tack and poorer shear stability.

The glass transition temperature is that temperature at which amorphous or partially crystalline polymers undergo transition from the liquid or rubber-elastic state into the hard-elastic or glassy state, or vice versa (Rompp Chemie-Lexikon, 9th Ed., Volume 2, page 1587, Georg Thieme Verlag Stuttgart—New York, 1990). It corresponds to the maximum of the temperature function at a predetermined frequency.

For medical applications in particular, a relatively low glass transition point is required.

| Designation | $T_g$ low frequency | Conformity low frequency/RT | Tack high frequency/RT |
|---|---|---|---|
| Hotmelt adhesive composition A | −12 ± 2° C. | tan δ = 0.32 ± 0.03 | tan δ = 1.84 ± 0.03 |
| Hotmelt adhesive composition B | −9 ± 2° C. | tan δ = 0.22 ± 0.03 | tan δ = 1.00 ± 0.03 |

The hotmelt adhesive compositions are preferably formulated such that their dynamic-complex glass transition temperature at a frequency of 0.1 rad/s is less than 15° C., preferably from 0 to −30° C. and, with very particular preference, from −3 to −15° C.

Preference is given in accordance with the invention to hotmelt adhesive compositions for which the ratio of the viscous component to the elastic component at a frequency of 100 rad/s at 25° C. is greater than 0.7, in particular between 1.0 and 5.0, or to hotmelt self-adhesive compositions for which the ratio of the viscous component to the elastic component at a frequency of 0.1 rad/s at 25° C. is less than 0.4, preferably between 0.35 and 0.02 and, with very particular preference between 0.3 and 0.1.

It is advantageous, especially for the use of the backing material in medical products, for the adhesive composition to be applied partially to the backing material, by means for example of halftone printing, thermal screen printing, thermal flexographic printing or intaglio printing, because backing materials which have been adhesively treated in a continuous applied line may under adverse circumstances induce mechanical skin irritations when applied. Alternatively, application can be made by the nozzle method.

In a preferred embodiment, the self-adhesive composition is applied to the backing in the form of polygeometric domes, especially those where the ratio of diameter to height is less than 5:1. The domes can take various forms. Flattened hemispheres are preferred. Printed application of other forms and patterns on the backing material is also possible—for example, a printed image in the form of alphanumeric character combinations or patterns such as matrices, stripes, assemblies of domes, and zig-zag lines.

In addition, for example, the composition can be applied by spraying, so producing a more or less irregular application pattern.

The adhesive composition can be distributed uniformly over the backing material; alternatively, it can be applied with a thickness or density which varies over the area, as is appropriate for the function of the product.

The dome geometry of the invention achieves a saving on adhesive composition in comparison to a conventional partially coated backing material, for a given contact area with the substrate, and greater adhesion to the substrate for a given applied weight of adhesive composition.

At the same time there is substantially no adverse effect on the advantageous, high permeability of the adhesive film for air and water vapour for special applications, especially in the medical sector.

The preferred process for producing a self-adhesively treated backing material features a total of three process steps.

In the first step, the geometric structures formed from hotmelt adhesive composition are applied to an auxiliary support by means of halftone printing, thermal screen printing or intaglio printing, or by the nozzle technique, in the second step the auxiliary support with these structures is guided onto the backing material, and, finally, the structures are transferred from the auxiliary support onto the backing material.

The term auxiliary supports is to be understood as meaning conventional, endless webs of various materials, but also apparatus such as rolls.

Depending on the backing material and its temperature sensitivity, the hotmelt adhesive composition can, however, be applied directly to the backing material. Subsequent calendering of the coated product and/or pretreatment of the backing, such as corona irradiation, for better anchorage of the adhesive layer may also be advantageous.

In addition, treatment of the hotmelt adhesive composition by electron-beam postcrosslinking or by UV irradiation may result in an improvement in the desired properties.

The principle of thermal screen printing consists in the use of a rotating, heated, seamless, drum-shaped, perforated, cylindrical screen which is fed via a nozzle with the preferred hotmelt adhesive composition. A specially shaped nozzle lip (circular-gap or square-section coating bar) presses the hotmelt adhesive composition, which is fed in via a channel, through the perforation of the screen wall and onto the backing web that is conveyed past it. This backing web is guided by means of a counter roller against the external jacket of the heated screen drum at a rate which corresponds to the peripheral speed of the rotating screen drum.

In this process, the formation of the small domes of adhesive takes place by the following mechanism:

The pressure of the nozzle coating bar conveys the hotmelt adhesive composition through the screen perforation onto the backing material. The size of the domes formed is defined by the diameter of the screen perforation. The screen is lifted from the backing in accordance with the rate of transportation of the backing web (rotary speed of the screen drum). As a consequence of the high adhesion of the adhesive composition and of the internal cohesion of the hotmelt, the limited supply of hotmelt adhesive composition in the perforations is drawn in sharp definition from the base of the domes, which is already adhering to the backing, and is conveyed onto the backing by the pressure of the coating bar.

Following the end of this transportation, the more or less highly curved surface of the dome forms over the predefined base area in dependence on the rheology of the hotmelt adhesive composition. The height-to-base ratio of the dome depends on the ratio of the perforation diameter to the wall thickness of the screen drum and on the physical properties (flow behaviour, surface tension and contact angle on the backing material) of the self-adhesive composition.

For the screen in thermal screen printing the web-to-hole ratio can be less than 10:1, preferably less than or equal to 1:1, and, in particular, equal to 1:5.

The above-described mechanism of formation of the domes requires, preferentially, backing materials that are absorbent or at least wettable by hotmelt adhesive composition. Non-wetting backing surfaces must be pretreated by chemical or physical methods. This can be done by means of additional measures such as corona discharge, for example, or by coating with substances which improve wetting.

Using the printing technique indicated it is possible to lay down the size and shape of the domes in a defined manner. The bond strength values which are relevant for use, i.e. those which determine the quality of the products formed, are within very narrow tolerances provided that coating is carried out correctly. The base diameter of the domes can be chosen to be from 10 to 5000 $\mu$m, the height of the domes from 20 to 2000 $\mu$m, preferably from 50 to 1000 $\mu$m, the low-diameter range being intended for smooth backings and the range of greater diameter and greater dome height being intended for rough or highly porous backing materials.

The positioning of the domes on the backing is laid down in a defined manner by the geometry of the applicator unit, for example the gravure or screen geometry, which can be varied within wide limits. With the aid of the parameters indicated it is possible, by way of adjustable variables, to establish with very great precision the desired profile of properties of the coating, harmonized with the various backing materials and applications.

The backing material is preferably coated at a rate of more than 2 m/min, preferably from 20 to 200 m/min, the chosen coating temperature being greater than the softening temperature.

The percentage area that is coated with the hotmelt adhesive composition should be at least 20% and can range up to approximately 95%, for specific products, preferably from 40 to 60% and from 70 to 95%. This can be achieved, if desired, by means of multiple application, with the possible use if desired of hotmelt adhesive compositions having different properties.

A controlled temperature regime and/or the introduction of radiative, mechanical or secondary energy during production make it possible in the case of thermoplastic self-adhesive compositions to modify the geometry of the geometric structures, it being possible to vary the head diameter and base diameter within wide limits.

Preferably, a controlled temperature regime can also be operated on the surface of the thermoplastic or elastic primary domes, i.e. the domes applied to the auxiliary support, this regime being brought about, for example, by radiative heating, such as IR, by means of which it is possible to generate secondary domes having the optimum bond properties for product transfer.

An addition in connection with the control of energy in the material and/or on the surface of the polymers permits a great diversity of polygeometric dome forms. For the ultimate shaping of the transferred secondary dome, it may be advantageous to have a regulatable printing station (gap/pressure/temperature/speed). Subsequent calendering may also be advantageous.

The profile of viscoelastic properties, present prior to the transfer of the secondary dome, of the structures formed from self-adhesive composition can be 30 adjusted by controlling the thermal energy from the coating process, by the at least partial introduction of surface energy, or by the at least partial removal of thermal energy, or by a combination of the techniques.

The geometric structures can, accordingly, be divided into a plurality of zones which may have entirely different characteristics. The geometric structures applied to the auxiliary support, at the time of transfer to the backing material, preferably have—in the base zone, which corresponds to that part of the structure which lies against the backing material—a plasticity/elasticity ratio at a frequency of 100 rad/s of from 0.4 to 50 and—in the head zone, which constitutes the external part of the structure opposite to the base zone—a plasticity/elasticity ratio of greater than 0.3, preferably from 0.4 to 50, with the plasticity/elasticity ratio in the head zone not being smaller than that in the base zone.

It has also been found to be advantageous for the height ratio of head zone to base zone to be established at between 5 and 95%, preferably between 10 and 50%.

The combination of the hotmelt adhesive composition and the partial coating ensures secure bonding of the backing material. Especially when the backing material is used to produce a medical product, this product adheres to the skin and, on the other hand, allergic or mechanical skin irritations—at least those which are visually discernible—are prevented, even in the case of an application which extends over several days.

Partial application makes it possible, through controlled channels, to dissipate the transepidermal water loss, and improves the removal of perspiration from the skin in vapour form, especially when the backing materials used are permeable to air and water vapour. By this means skin irritations induced by accumulation of body fluids are prevented. The dissipation channels that have been set up enable fluids to be conducted away, even when a multi-ply dressing is used.

The epilation of corresponding body regions and the transfer of composition to the skin are negligible owing to the high cohesiveness of the adhesive, since the adhesive is not anchored to skin and hair—rather, the anchorage of the adhesive composition to the backing material, at up to 12 N/cm (sample width) is good for medical applications.

Because of the intended breakage points that have been formed in the coating, layers of skin are no longer displaced with one another or against one another in the course of detachment. The non-displacement of the layers of skin and the relatively low level of epilation lead to an unprecedented degree of painlessness in such strongly adhering systems. In addition, the individual biomechanical control of bond strength, which exhibits a demonstrable reduction in the bond strength of these plasters, assists detachability. The applied backing material shows good proprioreceptive effects.

In a further advantageous embodiment, the self-adhesive compositions are foamed before being applied to the backing material.

In this case the self-adhesive compositions are preferably foamed using inert gasses, such as nitrogen, carbon dioxide, noble gasses, hydrocarbons or air, or mixtures thereof. In some cases, foaming additionally by thermal decomposition of gas-evolving substances, such as azo, carbonate and hydrazide compounds, has been found to be suitable.

The degree of foaming, i.e. the gas content, should be at least about 5% by volume and can range up to about 85% by volume. In practice, levels of from 10 to 75% by volume, preferably 50% by volume, have been found to be appropriate. Operating at a relatively high temperature of approximately 100° C and with a comparatively high internal pressure produces very open-pored adhesive foam layers which are particularly permeable to air and water vapour.

The advantageous properties of the foamed self-adhesive coatings, such as low consumption of adhesive, high tack and good conformity, even on uneven surfaces, owing to the elasticity and plasticity, and also the initial tack, can be utilized to best effect in the field of medical products.

The use of breathable coatings in conjunction with elastic and likewise breathable backing materials produces a level of wear comfort which is perceived subjectively by the user as more pleasant.

A particularly suitable method of preparing the foamed self-adhesive composition operates by the foam mixing system. In this system, the thermoplastic self-adhesive composition is reacted with the intended gasses, such as nitrogen, air or carbon dioxide, for example, in various volume proportions (from about 10 to 80% by volume) in a stator/rotor system under high pressure and at a temperature above the softening point (approximately 120° C.).

While the gas entry pressure is greater than 100 bar, the mixing pressures between gas and thermoplastic in the system are from 40 to 100 bar, preferably from 40 to 70 bar. The pressure-sensitive adhesive foam produced in this way can subsequently be passed through a line into the applicator unit. In the applicator unit, commercially customary nozzles, extruder systems or chamber systems are used.

By virtue of the foaming of the self-adhesive composition and of the open pores in the composition which form as a result, and given the use of an inherently porous backing, the products coated with the adhesive composition have good permeability to water vapour and air. The amount of adhesive composition required is considerably reduced without adverse effect on the adhesion properties. The adhesive compositions have a surprisingly good tack, since per gram of composition there is more volume and thus more adhesion surface for wetting of the substrate that is to be bonded, and the plasticity of the adhesive compositions is increased by the foam structure. Anchorage to the backing material is also improved in this way. The foamed adhesive coating, moreover, gives the products a soft and conforming feel, as has been mentioned above.

Foaming also reduces the viscosity, in general, of the adhesive compositions. This lowers the melt energy, and even thermally unstable backing materials can be coated directly.

The hotmelt adhesive composition can be applied to the backing material with an area weight of greater than 6 g/m$^2$, preferably between 20 and 300 g/m$^2$, and with very particular preference, between 40 and 180 g/m$^2$.

The backing material coated with the adhesive composition can have an air permeability of greater than 1 cm$^3$ (cm$^2$*s), preferably greater than 15 cm$^3$/(cm$^2$*s), and, with very particular preference, greater than 70 cm$^3$/(cm$^2$*s), and a water vapour permeability of greater than 200 g/(m$^2$*24 h), preferably greater than 500 g/(m$^2$*24 h), and, with very particular preference, greater than 2000 g/(m$^2$*24 h). The bond strength of the backing material of the invention to the reverse of the backing is at least 0.5 N/cm, in particular between 2.5 and 5 N/cm. Higher bond strengths may be achieved on other substrates.

The outstanding properties of the backing material of the invention that has been given a self-adhesive treatment suggests its use for medical products, especially plasters, medical fixings, wound coverings, doped systems, orthopaedic or phlebological bandages and dressings. In the case of the doped systems, particular preference is given to those which release substances.

Finally, the backing material following the coating operation can be lined with an anti-adhesive backing material, such as siliconized paper, or provided with a wound pad or padding.

It is particularly advantageous that the backing material can be sterilized, preferably by means of γ-(gamma) radiation. Consequently, particular suitability for subsequent sterilization is possessed by block copolymer-based hotmelt adhesive compositions which contain no double bonds. This applies in particular to styrene-butylene-ethylene-styrene block copolymers or styrene-butylene-styrene block copolymers. In this case the adhesive properties are not subject to any changes significant for the application.

The backing material is also outstandingly suitable for technical reversible fixings which on removal cause no damage to a variety of substrates, such as paper, plastics, glass, textiles, wood, metals or minerals.

Finally, it is possible to produce technically permanent bonds, which can be separated only with partial splitting of the substrate.

With reference to a number of figures, advantageous embodiments of the subject-matter of the invention will now be described, without wishing thereby unnecessarily to restrict the invention.

Of these figures,

FIG. 1 shows a section taken from a continuous backing material 1 coated with essentially hemispherical domes 2.

Figure 1:
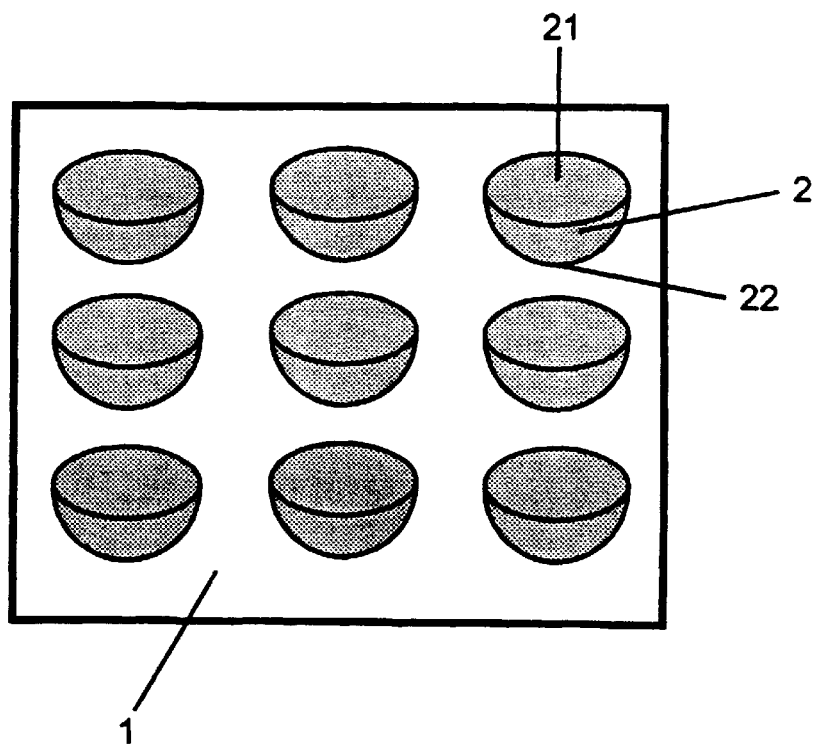
FIG. 1 shows a backing material coated with hemispherical domes.

Within each individual dome 2 it is possible to make out a base zone 22, which lies in the region of the dome 2 at which the dome 2 is anchored to the backing material 1, and the head zone 21, which is opposite to the base zone 22. The two zones 21 and 22, can if desired have characteristics which deviate from one another.

Figure 2:
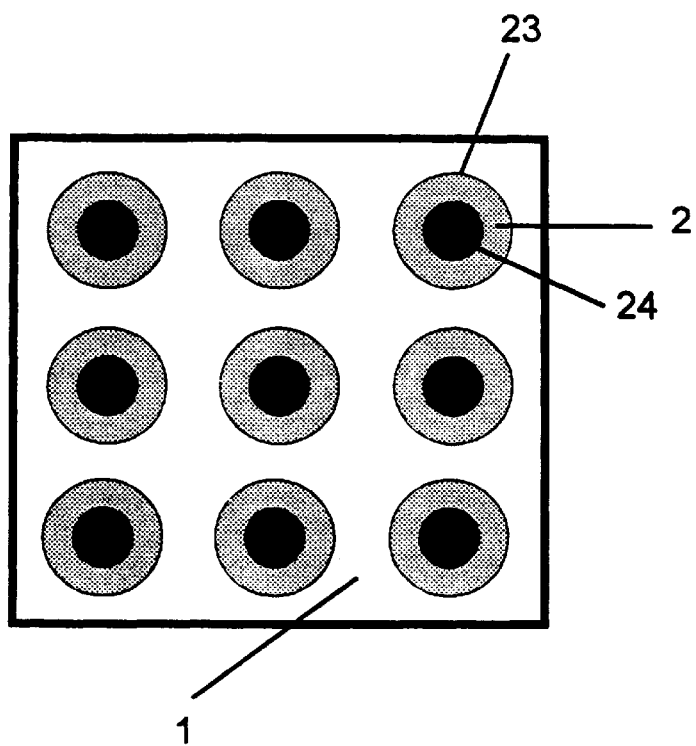
FIG. 2 shows the coated backing material of FIG. 1 in plan view.

FIG. 2, which shows the coated backing material of FIG. 1 in plan view, serves to illustrate the base area 24 and the projection area 23 The base area 24 is that area of the dome 2 by which the dome is anchored to the backing material 1. The projection area 23 is the area which results from a perpendicular projection of the dome 2 onto the backing material 1. In accordance with the invention, the domes 2 are always formed in such a way that the base area 24 lies within the projection area 23.

Figure 3:
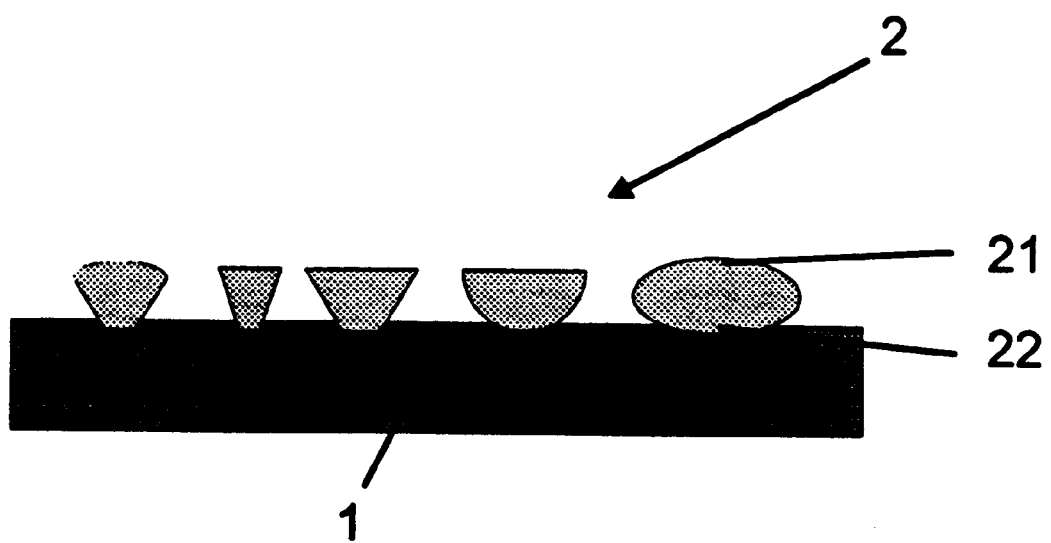
FIG. 3 shows, in lateral section, a backing material coated with different-shaped domes.

In FIG. 3, finally, different-shaped domes 2 are shown in lateral section, these domes having been found to be particularly advantageous. The base zone 22 and the head zone 21, again, can be seen particularly clearly on the right-hand dome.

In the text below a backing material of the invention which has been given a self-adhesive treatment is illustrated by means of an example, again without wishing unnecessarily to restrict the invention.

EXAMPLE 1

In accordance of the invention, a non-elastic self-adhesive bandage was produced which owing to its properties, described below, can be used as a functional tape dressing, the functional dressing technique being guided by the anatomy and biomechanics. The bandage used for this type of dressing consisted of a non-elastic woven cotton fabric with a breaking strength of more than 60 N/cm and a breaking extension of less than 20%.

The self-adhesive composition was applied to the backing by thermal screen printing, and was a hotmelt self-adhesive having the following composition:

an A-B/A-B-A block copolymer consisting of hard and soft segments, with a ratio of A-B-A to A-B of 2:1 and a styrene content in the polymer of 13 mol %; its proportion in the adhesive composition is 40% by weight (Kraton G)

a paraffinic hydrocarbon wax whose proportion in the adhesive composition is 45% by weight hydrocarbon resins with a proportion of 14.5% by weight (Super Resin HC 140)

an anti-ageing agent with a proportion of less than 0.5% by weight (Irganox)

The components employed were homogenized in a thermal mixer at 195° C.

The softening point of this adhesive composition was about 85° C. (DIN 52011), and the adhesive composition had a viscosity of 2100 mPas at 150° C. (DIN 53018, Brookfield DV II, sp. 21). The glass transition according to the method set out above was −7° C.

The PSA geometry of the invention was realized by means of the above-described transfer of the PSA domes from an auxiliary support onto the backing material:

The indirect coating took place at 50 m/min and at a temperature of 120° C. onto a pretreated counter-pressure roller (auxiliary support) and from there onto the backing material.

Shortly before the backing material was introduced, energy was supplied by irradiation of the adhesive composition. This lead to a division of the dome of adhesive composition adhering to the auxiliary support into a head zone of high plasticity and low elasticity and a base zone of low plasticity and high elasticity. A transition zone was established in between.

Under pressurized transfer onto the textile backing material, the low-viscosity head zone penetrated readily into the backing material where it provided good anchorage of the dome of adhesive composition; the high-viscosity base zone laid itself onto the backing material and prevented excessive penetration of the pressure-sensitive adhesive into the backing material.

It has been found advantageous to bring the entire PSA hotmelt domes, before transfer, into the desired viscoelastic state of the base zone or to obtain this state from the heat of fusion, and to bring only the head zone into the desired low-viscosity state by means of a short pulse of radiation directly prior to transfer.

The backing material was coated with 120 g/m², using a 14 HX mesh screen stencil.

The base of the dot was 5% less in area than the head of the dot. This produced more stable bonding of the dots, since there was no edge corner on the bond area of the adhesive sheet-like structure.

Owing to the transfer from the smooth auxiliary support, moreover, the surface of the adhesive composition acquired a planar surface which was likewise suitable for enlarging the contact area with planar substrates.

The bond strength to the reverse of the backing was 15% greater than that of a comparison sample with the same mass application.

The bandage produced by this method exhibited reversible detachment from the skin and good permeability to air and water vapour. Because of the high shear stability of the hotmelt pressure-sensitive adhesive, sufficient stabilization and a good proprioreceptive effect were found. No skin irritations, and a negligible degree of epilation, were observed after the bandage had been removed.

What is claimed is:

1. A process for producing a backing material having a partial coating of a hotmelt self-adhesive composition on at least one side, said partial coating of self-adhesive composition being in the form of geometric structures wherein
   a) geometric structures are formed from hotmelt adhesive composition and are applied by halftone printing, thermal screen printing or intaglio printing, or by the nozzle method, to an auxiliary support,
   b) the auxiliary support with the geometric structures applied thereto is guided onto a backing material, and
   c) the geometric structures are transferred from the auxiliary support to the backing material.

2. Process according to claim 1, wherein the geometric structures are modified by a controlled temperature regime, by the introduction of radiative, mechanical or secondary energy, or by both.

3. Process according to claim 1, wherein the profile of the viscoelastic properties of the geometric structures is adjusted by controlling the thermal energy from the coating process, by the at least partial introduction of surface energy or by the at least partial removal of thermal energy, or by a combination of said methods.

4. Process according to claim 1, wherein the geometric structures applied to the auxiliary support, at the time of transfer onto the backing material, have, in the head zone, a plasticity/elasticity ratio at a frequency of 100 rad/s of greater than 0.3, and, in the base zone, a plasticity/elasticity ratio of from 0.4 to 50, the plasticity/elasticity ratio in the head zone being not lower than that in the base zone.

5. Process according to claim 1, wherein the height ratio of head zone to base zone is established at between 5 and 95%.

6. Process according to claim 1 wherein the hotmelt adhesive composition is foamed.

7. Process according to claim 1, wherein the hotmelt adhesive composition is crosslinkable by UV or electron beam irradiation.

* * * * *